United States Patent [19]
Sahm et al.

[11] 3,974,172
[45] Aug. 10, 1976

[54] BENZOFURAN DERIVATIVES

[75] Inventors: Wilfried Sahm, Kelkheim, Taunus; Erich Schinzel, Hofheim, Taunus; Günter Rösch, Altenhain, Taunus, all of Germany

[73] Assignee: Hoechst Aktiengesellschaft, Frankfurt, Germany

[22] Filed: Feb. 6, 1974

[21] Appl. No.: 440,013

[30] Foreign Application Priority Data
Feb. 9, 1973 Switzerland.......................... 1879/73

[52] U.S. Cl. .................. 260/307 D; 260/240 R; 260/240 D; 260/240 CA; 260/240.6; 252/301.22; 252/301.28
[51] Int. Cl.² .................................... C07D 263/56
[58] Field of Search ............... 260/307 D

[56] References Cited
UNITED STATES PATENTS
3,772,323  11/1973  Schlapfer et al................. 260/309.2

*Primary Examiner*—Raymond V. Rush
*Attorney, Agent, or Firm*—Connolly and Hutz

[57] ABSTRACT

Benzofuran compounds of the formula

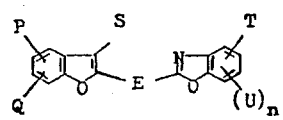

wherein E is a bivalent bridging member of the formula

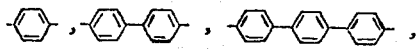

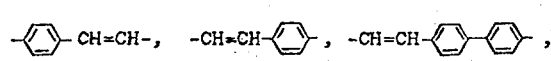

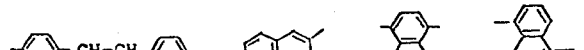

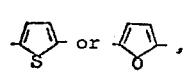

S is hydrogen, halogen, lower alkyl, carboxy, sulfo, cyano, lower carboalkoxy, carbonamido, lower mono- or dialkyl carbonamido, sulfonic acid lower alkyl ester, sulfonamido, lower mono- or dialkyl sulfonamido or phenyl; P, Q, T and U are hydrogen or halogen, lower alkyl, lower alkoxy, phenyl, carboxy, cyano, lower carboalkoxy, lower carbo-alkoxy substituted by a member selected from the group consisting of lower alkoxy, lower dialkylamino and lower trialkyl ammonium, carbonamido, lower mono- or di-alkyl carbonamido, sulfo, sulfonic acid lower alkyl ester, sulfonamido or lower mono- or dialkyl sulfonamido or P and Q together or T and U together are lower alkylene or an annellated phenyl ring, and $n$ is 1 to 3. These compounds can be synthetized by a condensation reaction of the corresponding carboxylic acid derivative with an ortho-aminophenol or by HORNER or similar syntheses forming said bridging member. The products are optical brighteners.

2 Claims, No Drawings

BENZOFURAN DERIVATIVES

The present invention relates to new benzofuran derivatives, a process for their preparation and their use as optical brighteners.

It is known to prepare benzofuran derivatives which are linked over the carbon atom (2) of the benzofuran nucleus with a direct bond to a benzoxazole ring (German Offenlegungsschrift No. 2,031,774).

This invention provides new colorless to weakly yellow benzofuran derivatives which have in solution a blue fluorescence of a violet to a greenish blue tinge and which correspond to the formula (1)

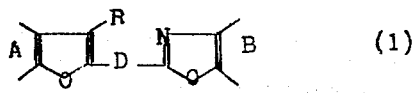

in which formula
A and B each is an identical or different aromatic, mono or polynuclear ring system which has two adjacent carbon atoms in common with the furan and oxazole nucleus in the manner indicated,
R is a hydrogen or halogen atom, a lower alkyl group, a phenyl group optionally substituted by lower alkyl, lower alkoxy groups or by halogen atoms and an optionally functionally modified carboxy or sulfo group,
D is a completely conjugated chain of carbon atoms which may be wholly or in part a constituent of a carbocyclic or heterocyclic ring system, and which is conjugated with the ajacent double bonds of the furan and oxazole rings, with the proviso that D contains at least
2 C—C-double bonds or at least 1 C—C-triple bond.

The terms "lower" or "low-molecular" in connection with aliphatic groups imply radicals of up to 4 carbon atoms, e.g. alkyl groups of 1 to 4 carbon atoms or alkenyl groups of 2 to 4 carbon atoms.

To the aromatic ring systems A or B non chromophorous substituents may be bound, for example, preferably low molecular weight alkyl, alkenyl or alkoxy groups, aryl groups optionally modified carboxy or sulfo groups, acyl, acylamino or sulfonyl groups and halogen atoms. Several of these groups which are identical or different may also be linked to A or B at the same time.

In the definitions given above for A, B and R, a functionally modified carboxy group is, primarily, its salt with a colorless cation, alkali metal ions or ammonium ions being preferred. There may, furthermore, especially be mentioned the cyano group (nitrile group), the carboxylic acid ester group or the carboxylic acid amide group. carboxylic ester groups are especially those of the general formula $COOR^1$, wherein $R^1$ is a phenyl radical or a lower alkyl group optionally having a branched chain, which radicals may contain further substituents, for example, a preferably low-molecular dialkylamine, lower trialkylammonium or lower alkoxy group in which dialkylamino or trialkylammonium groups two alkyl groups may together with the nitrogen atom form a ring, such as in the morpholino or piperidino groups. A carboxylic acid amide group is especially one of the formula $CONR^2R^3$ wherein the radicals $R^2$ and $R^3$ each represents a hydrogen atom or a lower alkyl group which may, optionally, be substituted, and which may also form together with the nitrogen atom a hydroaromatic ring, especially the piperidino or morpholino ring, moreover acid hydrazides of the formula $CONHNR^2R^3$ in which $R^2$ and $R^3$ are defined as above, and the analogous thio derivatives.

Functionally modified sulfo groups are, in analogy to the description given above, the salts with colorless cations, preferably alkali metal ions or ammonium ions, and derivatives in which the $SO_2$-group is linked to a hetero atom, as to be found in the sulfonic acid ester group and in the sulfonamide group. A sulfonic acid ester group is especially one of the formula $SO_2OR^1$ in which $R^1$ is defined as above and a sulfonamide group is one of the formula $SO_2NR^2R^3$ in which $R^2$ and $R^3$ are defined as above.

An acyl group is especially one of the formula $COR^4$ in which $R^4$ stands for a preferably lower alkyl or phenyl radical optionally substituted by non chromophorous radicals.

A sulfonyl radical is especially one of the formula $SO_2R^5$ in which $R^5$ stands for a lower alkyl or phenyl group optionally substituted by non chromophorous radicals, in which case these groups may contain as substituents preferably a lower dialkylamino, lower trialkyl-ammonium, acylamino or sulfo group.

Among the compounds of the general formula (1) especially those corresponding to the general formula (2)

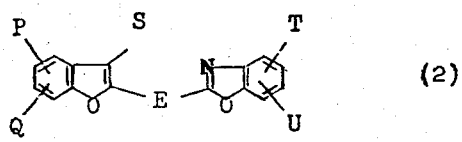

in which E is one of the following groups

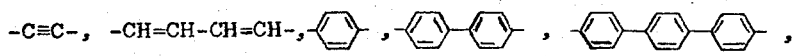

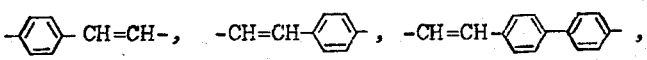

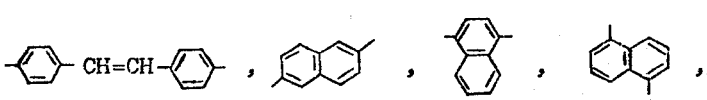

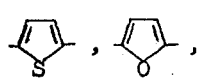

S stands for a hydrogen or halogen atom, a sulfonic acid and a sulfonic acid mono or dialkylamide group having 1 to 4 carbon atoms in the alkyl groups, an optionally functionally modified carboxy group, a lower alkyl, preferably a methyl group, and the phenyl group, P and Q and T and U each stands, independent from one another, for a hydrogen or halogen atom, lower alkyl, lower alkoxy or phenyl groups, optionally functionally modified carboxy or sulfo groups or P and Q and T and U together stand for a lower alkylene group or an annellated benzene nucleus.

Especially compounds which fluoresce within the range of from about 410 to about 450 nm are preferred.

The compounds of the invention may be synthesized according to the preparation processes described hereinafter, in which the radicals A, B, R and D in the formulae (3), (4), (5) are defined as in formula (1).

A preferred embodiment of the process of the invention consists in reacting a carboxylic acid or a reactive derivative thereof of the general formula

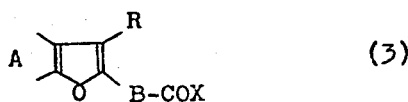

(3)

in which X stands for the hydroxy group or a halogen atom, especially a chlorine atom, with an o-aminophenol of the general formula (4)

(4)

at a temperature ranging from about 150°C to about 250°C, preferably at about 190° to about 220°C either by isolating the acyl-amino compounds of the general formula (5)

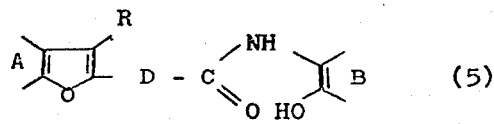

(5)

or directly preparing therefrom the oxazole compound of the formula (1) of the invention by splitting off 1 mol water.

The ring closure of the compounds (5) can be carried out by merely heating or by heating in a high boiling solvent or mixture of solvents in the presence of a catalyst.

High boiling solvents are, for example, chlorinated aromatic hydrocarbons, for example, dichlorobenzenes, trichlorobenzenes or α-chloronaphthalene and high boiling carboxylic acid esters, for example lower alkyl esters of the benzoic acid.

Suitable catalysts are, advantageously, Lewis acids, for example, $ZnCl_2$ or $AlCl_3$, mineral acids, for example, polyphosphoric acid or also organic sulfonic acids, for example, p-toluene-sulfonic acid.

The direct reaction of 1 mol of the carboxylic acids of the general formula (3) (X=OH) with 1 mol of the aminophenols of the general formula (4) to yield the oxazoles of the invention of the formula (1) is also possible when the components are heated in the presence of acid catalysts, for example, boric acid, in inert organic solvents, for example, those mentioned above, or in mixtures of these solvents until the water has completely split off. The compounds of the formula (1) may also be prepared by heating 1 mol of the carboxylic acids of the formula (3) (X=OH) with 1 mol of the aminophenols of the formula (4) in polyphosphoric acid to 120°–200°C.

As o-aminophenols of the formula (4) may be used, for example:

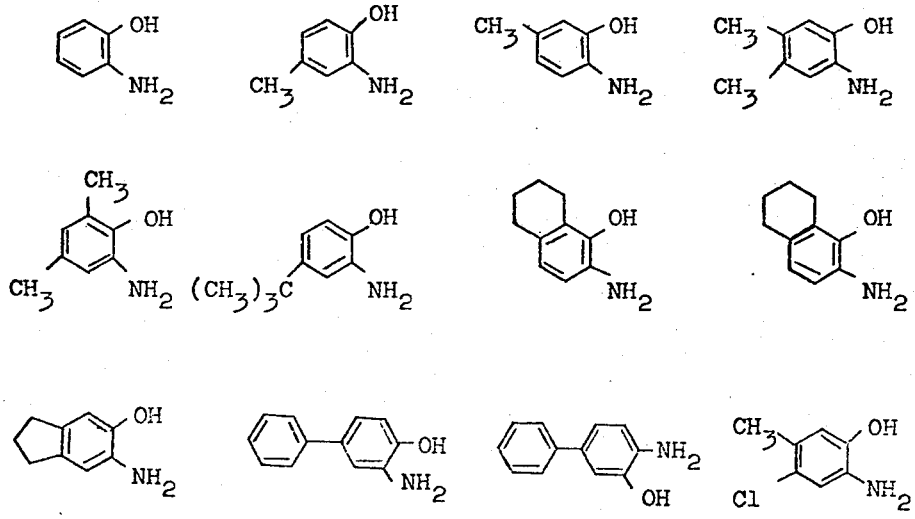

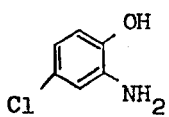 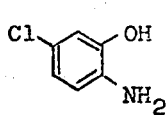 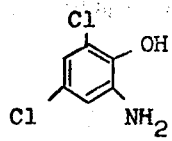

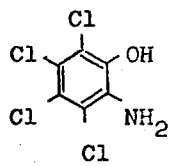 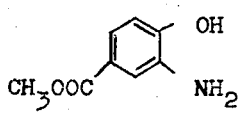 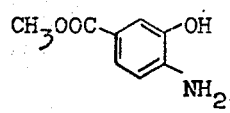

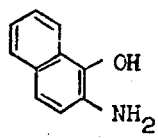 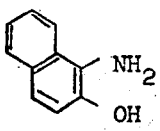 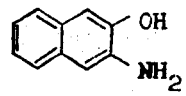

As carboxylic acids of the formula (3) (X=OH) and derivatives thereof, may be used, for example:

foregoing formulae, one of the following substituted benzofuran nuclei is contained:

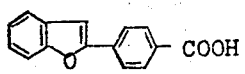 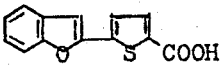 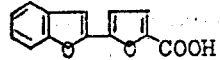

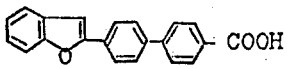 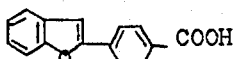 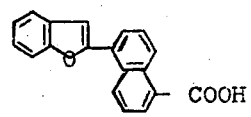

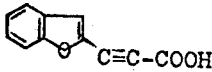 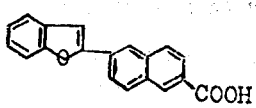

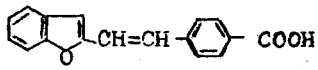

Moreover, carboxylic acids and the reactive derivatives thereof to be used are those in which, instead of the unsubstituted benzofuran nucleus indicated in the foregoing formulae, one of the following substituted benzofuran nuclei is contained:

The compounds in which the middle component D contains an olefinic double bond may be prepared not only according to the methods described, but also by

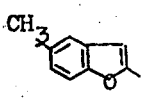 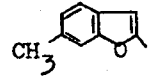 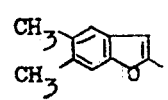 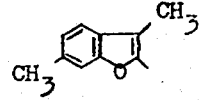

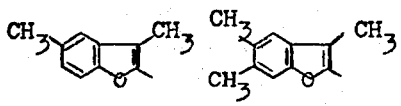 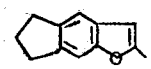

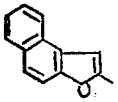 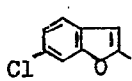 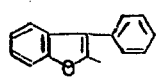

intermolecularly condensing either 1 mol of an aldehyde of the general formula (6)

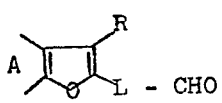 (6)

with 1 mol of a phosphorus compound of the general formula (7)

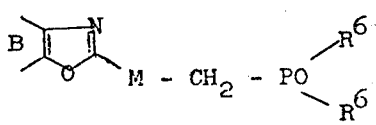 (7)

or 1 mol of an aldehyde of the general formula (8)

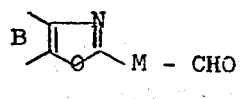 (8)

with 1 mol of a phosphorus compound of the general formula (9)

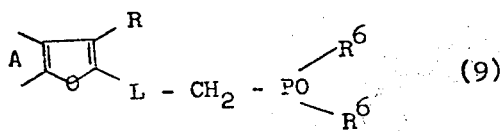 (9)

in an organic solvent or a mixture of solvents with the aid of strong bases.

In the general formulae (6) to (9) L and M which may be identical or different, stand for a direct bond or a completely conjugated chain of carbon atoms which may be, wholly or in parts, a constituent of carbocyclic or heterocyclic ring systems and which is conjugated with the adjacent double bonds of the furan and oxazole radicals.

The compounds obtained according to this process of the general formula (10)

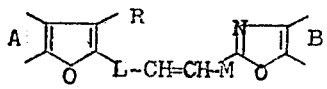 (10)

contain, as it can be seen, a middle component —L—CH=CH—M— which has the meaning of D, with the proviso that D contains at least one olefinic double bond.

$R^6$ stands for identical or different, preferably low-molecular alkyl, cycloalkyl or aryl radicals optionally linked to the phosphorus atom over an oxygen atom. As the radicals $R^6$ do not appear in the end product, their chemical nature is uncritical with respect to the product of the invention; however, lower alkyl groups, cycloalkyl groups of 4 to 8 carbon atoms or phenyl groups are preferred.

The process is advantageously carried out in inert solvents, for example, hydrocarbons, especially aromatic hydrocarbons, such as toluene or xylene, or alcohols, such as methanol, ethanol, isopropanol, butanol glycol, hexanol, cyclohexanol, cyclooctanol, moreover in ethers, such as diisopropyl ethers glycol ethers such as 2-methoxy ethanol, dioxane or tetrahydrofurane, moreover in formamides and N-methyl pyrrolidone. Especially suitable are dipolar organic solvents, for example, dimethyl formamide and dimethyl sulfoxide.

Suitable condensation agents are strongly basic compounds, for example, alkali metal or alkaline-earth metal hydroxides, alkali metal or alkaline-earth metal alcoholates, alkali metal or alkaline earth metal amides, preferably potassium hydroxide, sodium hydroxide, potassium tertiary butylate or sodium methylate, moreover the alkali metal compounds of dimethyl sulfoxide and alkali metal hydrides.

Depending on the nature of the starting compounds the reaction temperature ranges between about 0° to about 100°C, preferably between about 10° and about 80°C.

Naturally, other preparation processes can be used, for example those illustrated by the following formula scheme:

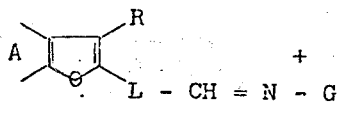 + 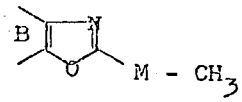

(11)               (12)

(10) ⇐  alkali
       ―――――――――――
       polar solvent

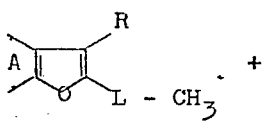 + 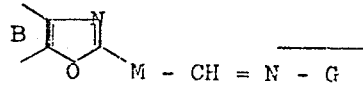

(13)               (14)

In the formulae (11), (12), (13) an (14) A, B, R, L and N are defined as in the general formula (10).

G stands for an aliphatic, aromatic carbocyclic or heterocyclic radical which is linked over a tertiary carbon atom to the azomethine nitrogen atom.

The azomethines of the general formulae (11) and (14) are prepared in a manner known per se from the carbonyl compounds and amines of the formula (15) from which they derive,

at normal or at elevated temperature and optionally with the use of solvents or diluents, for example, by heating in toluene, chlorobenzene or others, optionally in the presence of an acid catalyst, such as a mineral acid or a sulfonic acid.

Suitable amines of the formula (15) are, for example, anilines, naphthyl amines or, as aliphatic amine, tertiary butyl amine. As the amine radical, especially the aniline radical, is split off in the reaction, substituents generally are not favorable in this case. However, amines of the general formula (16)

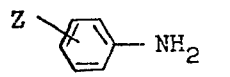

may be used, nevertheless, the phenyl radical of which carries substituents Z which do not hamper the reaction, for example, chlorine atoms.

Among the amines mentioned above which correspond to the general formula (15), the anilines of the general formula (16) in which Z stands for a hydrogen or a chlorine atom, are preferred. Among them, the unsubstituted aniline is especially preferred.

The condensation is carried out in strongly polar, neutral to alkaline organic solvents which are free from atoms, especially hydrogen atoms, capable of being replaced by alkali metals. The solvents especially used are alkylated acyl amides of the general formula (17)

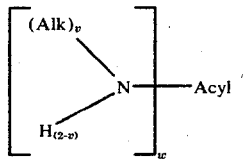

in which "Alk" is a lower alkyl group having up to four carbon atoms, "acyl' is the radical of a low molecular weight carboxylic acid having up to four carbon atoms — especially, formic acid and acetic acid — or the phosphoric acid radical, $w$ indicates the basicity of the acid and $v$ stands for 0, 1 or 2.

Moreover, the following solvents may successfully be used in special cases: tetramethyl urea, N-methylpyrrolidone, acetonitrile or pyridine.

However, the solvents which correspond to the general formula (17) are especially important. Compounds of the general formula 17 in which $v$ is 2 are preferred and among them, especially dimethyl formamide, hexamethyl phosphoric acid trisamide, diethyl formamide and dimethyl acetamide are interesting.

The solvents can be used along or as mixtures of solvents.

Moreover, a strongly basic condensation agent is needed for the reaction, such as strongly basic alkaline-earth metal compounds and especially alkali metal compounds, for example, the hydroxides, amides, hydrides, sulfides, alcoholates thereof and strongly basic ion exchangers.

Suitable alcoholates are, essentially, those which are derived from open-chained, branched or cyclic lower aliphatic alcohols having up to 8 carbon atoms, preferably alkanols having 1 to 4 carbon atoms.

The corresponding sodium or potassium compounds are preferably used and the hydroxides, amides and alcoholates thereof have a special practical importance. Mixtures of these bases may, of course, also be used.

The alkaline condensation agents are preferably used in at least the equivalent amount, but also, if necessary, a manyfold equivalent amount may be used especially if the compounds to be condensed contain groups capable of being hydrolized or if higher temperatures are required in which case part of the condensation agent may be consumed by reaction with the solvent.

Frequently, the reaction is carried out at room temperature without external heating, which especially occurs when using potassium alcoholates or potassium hydroxide. In some cases, it is advantageous or even necessary to heat the reaction mixture which is advantageously covered by nitrogen, slowly to 30°– 120°C and to maintain that temperature for a certain time.

The reaction products obtained according to the methods mentioned above may, of course, be further modified, for example, they can be sulfonated with sulfonated agents, for example, $H_2SO_4$, mixtures of $H_2SO_4$ and $SO_3$, chlorosulfonic acid or amidosulfonic acid, or in such a manner that, for example, starting from molecules containing sulfo or carboxy groups compounds are obtained which have functionally modified sulfo or carboxy groups or that these groups are converted to other groups of this type or to the free acids.

Moreover, for example, chloromethyl groups may be introduced or methyl groups be oxidized in known manner; likewise, halogenations and further reactions of the halogen atoms introduced are feasible, for example, the exchange of chlorine or bromine against the cyano group or amine functions.

Because of their fluorescing capability, the compounds of the invention may be applied in a wide application field, above all for the optical brightening of the most various synthetic, semi-synthetic and natural high-molecular weight materials.

Synthetic organic high molecular weight materials are polymerization, polycondensation and polyaddition products and the after-treatment products thereof, for example, polymers on the basis of $\alpha$, $\beta$-unsaturated carboxylic acids, olefin hydrocarbons or halogenated hydrocarbons (polyolefins, polyvinyl chloride, polyvinylidene chloride, polystyrene, polyacrylonitrile and others), polycondensates on the basis of bifunctional or polyfunctional compounds having groups capable for condensation and the homo and co-condensation products thereof (polyesters), polyamides, maleinate resins, polycarbonates, silicone resins and others), polyaddition products, for example, cross-linked or non-cross-linked poly-urethanes and epoxy resins.

Semi-synthetic organic materials are, for example, cellulose esters and ethers, nitrocellulose, regenerated cellulose and plastics on the basis of casein.

Natural organic materials which can be brightened optically are, for example natural polyamides, such as wool, silk and leather, cellulose materials, such as cotton or wood compositions in fine dispersion, furthermore caoutchouc, guttapercha or balata.

The organic materials to be brightened optically may have the most various processing states, for example, crude materials, semi-finished or finished articles, and aggregate states, for example, shaped articles such as plates, sheets, films and foils, ribbons, filaments, fibers, for example, in the form of endless threads, staple fibers, flocks, hanks, yarns, twists, fiber fleeces, felts, waddings, textile woven fabrics, sandwich materials and knitted fabrics; moreover, powders, chips, granules, foams, lacquers cements, pastes, waxes, adhesive and cement masses, etc.

The new optical brighteners may, of course, also be used whereever organic materials of the type described above are combined in any form with inorganic materials.

The compounds of the invention are, however, preferably used for the optical brightening of fibers, textiles and plastic materials.

Compounds of the invention which are insoluble in water are especially suitable for the optical brightening of polyester and polyamide fibers and may be applied as a solution in organic solvents or in aqueous dispersion, preferably with the use of dispersing agents. Suitable dispersing agents are, for example, soaps, polyglycol ethers, which are derived from fat alcohols, fat amines or alkyl phenols, sulfite cellulose waste liquors or condensation products of optionally alkylated naphthalene sulfonic acids with formaldehyde.

The water-soluble anionic compounds of the invention are especially suitable for the optical brightening of copolymers of acrylo-nitrile, especially of the copolymers available in commerce having a minimum content of about 85 % acrylonitrile.

Benzofurans of the general formula 1 may also be added to detergents which may contain the usual filling and auxiliary agents, such as alkali metal silicate, alkali metal polyphosphates and poly-meta phosphates, alkali metal borates, alkali metal salts of carboxymethyl cellulose, foam stabilizers, such as alkanol amides of higher fatty acids, or complex forming agents, such as soluble salts of ethylene-diamine-tetraacetic acid or diethylene-triamine-pentaacetic acid, as well as chemical bleaching agents, such as perborates or percarbonates. Very good results are also obtained using perborate containing detergents in the presence of perborate activators. The usual desinfection agents used in detergents do not adversely affect the brightening effects of the compounds of the invention, either.

The brightening of the fibrous material with the aqueous or organic brightening liquor is effected either according to the exhaustion method at temperatures preferably ranging from about 20° to about 150°C or under thermosoling conditions, under which the textile material is, for example, impregnated with the brightening solution or dispersion and squeezed between rollers to a residual moisture of about 50 to 120 %. Subsequently, the textile material is subjected for about 10 to about 300 seconds to a heat treatment, preferably using dry heat of about 120° to about 240°C. This thermosoling process may also be combined with other finishing operations, for example, the finishing with synthetic resins to obtain "easy care" properties.

Moreover, the compounds of the invention may be exposed to high molecular weight organic materials before or during their shaping. They may, for example, be added to the molding compositions when manufacturing films, sheets, ribbons or shaped articles or be dissolved in the spinning masses before spinning. Suitable compounds may also be added to the low molecular weight starting materials before polycondensation or polymerization, as in the case of polyamide-6, polyamide-6,6 or linear esters of the type the polyethylene glycol terephthalate.

Compounds of the invention which are substituted by one or, preferably, two carboxy or carboalkoxy groups may be linked to linear polyester molecules and synthetic polyamides over an ester or amide bond, if they are added to these materials or, preferably, to their starting compounds, under suitable conditions. Optical brighteners so anchored in the substrate by a chemical linkage are distiguished by an extraordinary good fastness to sublimation and to solvents.

Olefinically unsaturated compounds of the invention which contain at least one polymerizable olefinic double bond in addition to the fluorescing system may be used for the manufacture of fluorescing polymers or polymer mixtures by polymerizing them as such, while maintaining the fluorescing system, or in mixture with other monomer or polymer vinyl compounds. These fluorescing polymers may then be mixed with non fluorescing polymers. Polymers optically brightened in such a manner excel by a high degree of whiteness. Moreover, the chemical bond of the brightener molecules to the polymers provide high fastness to sublimation and to solvents.

The amount of the compounds of the invention to be used corresponding to the general formula (1), calculated on the weight of the material to be optically brightened, may vary within wide limits according to the field of application and the effect desired. It can easily be evaluated by simple preliminary tests as is generally within the range of from about 0.01 to about 2 %.

The following prescriptions and examples illustrate the invention, the temperatures being expressed in degrees Celsius (centigrades). Parts and percentages are by weight unless otherwise stated; the ratio of parts by weight to parts by volume is that of the kilogram to the litre.

PRESCRIPTION A 112.8 g 4-[benzofuryl-(2)-benzoic acid (101) (melting point: 301° to 302°) were suspended in 500 ml of chlorobenzene and mixed while stirring with 42 ml of thionyl chloride and 5 ml of dimethyl formamide (hereinafter called:DMF). The reaction mixture was heated to 80° for 3 hours, 5 g of active charcoal were added, heating to 115°– 120°, filtration and cooling of the filtrate followed. The mixture was stirred into the ice bath and the fair yellow crystallate was filtered with suction, it was washed with benzene and dried in vacuo.

Yield: 97.5 g of 4-[benzofuryl-(2)-]-benzoyl chloride (102), Melting point: 163° – 165.5°.

25.6 g of 4-[benzofuryl-(2)]-benzoyl chloride (102), 11 g of o-aminophenol and 13 g of N, N-dimethyl-aniline were heated in 300 ml of chlorobenzene during 60 minutes to 80° and then during 60 minutes to 110°. The crystallate filtered with suction after cooling was introduced into a mixture of 20 ml of conc. $H_2SO_4$ and 480 ml of water and treated with steam to eliminate the chlorobenzene. The mixture was filtered hot with suction and dried in vacuo at 60°. 27.3 g of the acylamino compound (103) were obtained which corresponded to the formula

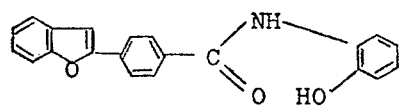

(103)

and melted at 227° – 228°.

27.3 g of the acylamino compound (103) were heated in 120 ml of trichlorobenzene with 0.3 g of p-toluenesulfonic acid during 75 minutes to about 210°, while 28 ml of a mixture of trichlorobenzene and water were distilled off during this period. After cooling the crystallate was filtered with suction, washed with methanol and dried in vacuo at 60°.

It was recrystallized from 600 ml of DMF whereupon 22.7 g of the compound 104 were obtained which melted at 283.5° λmax (absorption, in DMF): 349 nm, ε = 6.03 · 10⁴

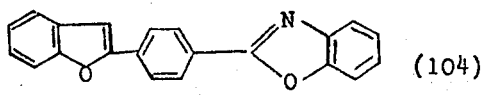
(104)

In an analogous manner or by further transformation of products which had been obtained according to the prescription A the compounds listed in the following table 1 were obtained.

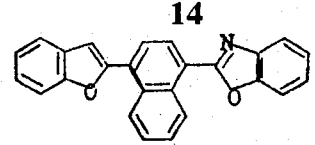
(119)

PRESCRIPTION C 8.5 g of (benzoxazolyl-2-methyl)-diethylphosphonate (120) (prepared from 2-chloromethyl-benzoxazole and triethylphosphite) and 5.2 g of β-benzofuryl-acrolein (121) (prepared from benzofuran-2-aldehyde and acetaldehyde by condensation in the presence of ethanolic KOH; melting point 65° – 67°, from cyclohexane) were dissolved in 30 ml of DMF and that solution was introduced in the course of 10 minutes at 30° – 40° into a suspension of 5 g of potassium tert.-butylate in 70 ml of DMF.

The mixture was stirred at room temperature for 45 minutes, poured onto 500 ml of ice water and neutralized with dilute hydrochloric acid. The precipitate was filtered with suction, washed portionwise with water

TABLE 1

| No. | A¹ | A² | B¹ | B² | B³ | B⁴ | melting Point (°C) | absorption λmax (nm) | ε · 10⁻⁴ | melting point (°C) of the acyl amino comp. |
|---|---|---|---|---|---|---|---|---|---|---|
| 105 | H | H | H | H | H | H | 282,5 – 283,5 | 349 | 6,03 | 227– 228 |
| 106 | H | H | H | COOCH₃ | H | H | 243– 257* | 350 | 6,01 | 282 – 283 |
| 107 | H | H | H | COOH | H | H | 354 – 358 | 350 | 5,19 | — |
| 108 | H | H | H | COOCH₂CH₂N(CH₃)₂ | H | H | 183 – 231* | 350 | 6,04 | — |
| 109 | H | H | H | C₆H₅ | H | H | 278– 280 | 353 | 6,58 | 271 – 273 |
| 110 | H | H | H | COOCH₂CH₂N(CH₃)₃⁺ CH₃OSO₃⁻ | H | H | — | 351 | 6,02 | — |
| 111 | H | H | H | CH₃ | CH₃ | H | 281,5 – 282 | 353 | 6,45 | 256 – 258 |
| 112 | H | H | H | Cl | CH₃ | H | 290 – 291 | 353 | 6,35 | 275 – 276 |
| 113 | H | H | Cl | Cl | Cl | Cl | 286 – 287,5 | 361 | 5,76 | 240 – 242 |
| 114 | CH₃ | CH₃ | H | H | H | H | 272 – 273 | 356 | 5,90 | 244 – 245,5 |
| 115 | CH₃ | CH₃ | H | CH₃ | CH₃ | H | 336,5 – 338 | 360 | 6,40 | 308,5 – 310 |
| 116 | H | OCH₃ | H | H | H | H | 211,5 – 212,5 | 362 | 5,31 | 218,5 – 219,5 |
| 117 | H | OCH₃ | H | CH₃ | CH₃ | H | 232,5 – 233,5 | 364 | 5,86 | 249 – 250,5 |

*liquid-crystalline behaviour

PRESCRIPTION B 14.4 g of 1-[benzofuryl-(2)]-naphthalene-(4)-carboxylic acid (118), 5.5 g of o-aminophenol and 0.7 g of boric acid were heated in 80 ml of trichlorobenzene to 210° to 212° during 120 minutes, while 10 ml of a mixture of trichlorobenzene and water were slowly distilled off. After cooling a small amount of insoluble substance was filtered off and the solvent removed from the filtrate. The residue was purified by column chromatography (Al₂O₃/benzene) whereupon 6.3 g of the compound (119) were obtained which melted at 155.5° after recrystallization from glacial acetic acid. λmax (absorption, DMF): 370 nm, ε = 3.31 · 10⁴.

until free from chlorine ions and dried. 7.55 g (87.6 % of the theory) of the compound (122) were obtained

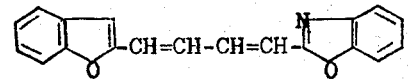

which melted at 192° – 193.5° (sintered at 190.5°) after several recrystalizations from n-butanol, λmax (absorption, DMF): 376 nm, ε = 6.2 · 10⁴.

EXAMPLE 1

1,000 Parts by weight of ε-caprolactam were melted at about 100° in a glass device continuously kept under nitrogen, provided with a steel stirrer and a descending cooler. Calculated on the amount of caprolactam used, 0.08 % by weight of the compound (109) and 0.34 % of a 12 % aqueous suspension of $TiO_2$ were added and the mixture was heated at 175° – 180° at first for 1 hour while stirring. After an hour, the mixture was heated to 275° and maintained at that temperature for about 5 hours. Towards the end of the reaction time an intensive nitrogen stream was fed in to distill off the excess amounts of lactam. The polyamide melt so prepared was extruded through a slot-die and the so-obtained band was quenched in water, chipped and dried.

A fabric obtained from this polycondensate by spinning and knitting showed a very much increased degree of whiteness having a good fastness to light as compared with a fabric manufactured in the same manner but to which no brightener had been added.

EXAMPLE 2

In a glass device provided with stirrer, a gas inlet pipe, a vacuum device and a descending cooler, 400 g of dimethyl terephthalate, 310 g of ethylene glycol and 0.5 g of anti-monoxide were heated under nitrogen to about 200° external temperature. This temperature was maintained during 3 hours, while slowly distilling off methanol. 0.4 g of the compound (106) and 20 g of a 20 % suspension of $TiO_2$ in ethylene glycol were added, the external temperature was raised to 285° and ethylene glycol was distilled off during 3 hours while slowly reducing the pressure to 0.2 torr. The block of optically brightened polyester material obtained in this manner after cooling was comminuted, granuled and, in the usual manner, spun to filaments or pressed to foils.

The filaments and foils so obtained showed a brilliant aspect and a good fastness to light.

EXAMPLE 3

Each 100 m of fabric made of polyethylene glycol terephthalate fibers of about 140 g/m² were impregnated with aqueous dispersions which contained 1.20 g/l of the compounds indicated in the following table 2. The pieces of fabric were then squeezed on a padding mangle. The residual liquid in the fabrics had about 60 % of the starting weight of the fabrics. The fabrics so treated were then thermosoled at 190° for 30 seconds in the tenter frame ("pad-thermosol-process").

The resulting degrees of whiteness evaluated are given in the following Table 2. The degrees of whiteness had been measured by means of the ELREPHO apparatus of Messrs. Zeiss, Oberkochen, at standardized type of light $D_{6000}$, and calculated according to the Berger formula $DW_B = Y + 3(\overline{Z} - \overline{X})$.

EXAMPLE 4

Each 2 kg of knit-wear made of texturized polyethylene glycol terephthalate fibers were treated with each 0.10 % calculated on the weight of the material, of the compounds indicated in Table 2. The compounds were used in dispersed form at a goods-to-liquor ratio of 1 : 20. The time of treatment was 45 minutes at a temperature of 120° ("high-temperature process"). The test results showed high brightening effects and a reddish-violet fluorescence. The degrees of whiteness measured are indicated in the following Table 2.

EXAMPLE 5

3 kg of polyacrylonitrile yarn were treated in a dyeing apparatus of the usual construction with 0.20 % of the dispersed compound (110). The goods-to-liquor ratio was 1 : 40, the pH value of the liquor was adjusted to 4.0 with oxalic acid. The liquor was heated from 30° to the boiling temperature within 30 minutes and the material was further treated at that temperature for a further 30 minutes. Finally, the material was rinsed several times as usual at a temperature gradually lowered and dried.

This operation method led to good brightening effects of high brilliance which are illustrated in the following Table 2.

EXAMPLE 6

Fabric pieces (50 kg each) made of cellulose-2 1/2-acetate were treated in an aqueous bath (goods-to-liquor ratio = 1 : 20) with 0.23 %, calculated on the weight of material, of the dispersed compounds (110) and (108). The temperature of treatment was 85°, the time of treatment was 60 minutes. As usual, rinsing and drying followed.

This treatment led to brightening effects the degrees of whiteness of which are contained in the following Table 2.

EXAMPLE 7

Each 50 g of fabric made of polyacrylonitrile yarn were treated in a liquor having the following composition:

1.2 g/l of sodium chlorite of 50 % strength,
0.5 g/l of a commercial bleaching auxiliary agent (on the basis of long-chain alkylaryl sulfonate),
0.2 g/l of acetic acid,
0.1 g/l of compounds (108) or (110).

The goods-to-liquor ratio was 1 : 20.

The material was introduced into the bath at 50°, the temperature of the bath was raised to 98° within 10 minutes and the material was treated at that temperature for 1 further hour. Then the fabric was rinsed and dried as usual.

Brilliant brightening effects were obtained with a fluorescence in reddish-violet range. The degrees of whiteness measured are shown in the following Table 2.

TABLE 2

| Brightener | Degrees of whiteness according to Berger | | | | |
| --- | --- | --- | --- | --- | --- |
| | Example 3 pad-thermosol-process on polyester | Example 4 high-temperature process on polyester | Example 5 exhaustion process on polyacrylonitrile | Example 6 exhaustion process on 2½acetate | Example 7 exhaustion process on polyacrylonitrile in the sodium chlorite bath |
| (105) | 108,5 | 127,4 | | | |
| (106) | 115,3 | 138,7 | | | |
| (108) | 109,7 | 123,3 | | 104,2 | 107,1 |
| (110) | — | — | 106,4 | 105,9 | 119,9 |
| (111) | 119,1 | 130,2 | | | |
| (112) | 115,9 | 127,7 | | | |
| (114) | 125,6 | 139,8 | | | |
| starting material unbrightened | 81,2 | 78,4 | 64,5 | 71,9 | 65,2 |

We claim:
1. A compound of the formula
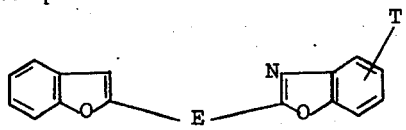
wherein E is p-phenylene and T is selected from the group consisting of 5-($\beta$-dimethylamino)-carboethoxy and 5-($\beta$-trimethylammonium)-carbo-ethoxy methosulfate.
2. The compound of claim 1 wherein R is 5-($\beta$-trimethylammonium)-carbo-ethoxy methosulfate.
* * * * *